United States Patent [19]
Draeger

[11] Patent Number: 5,203,331
[45] Date of Patent: Apr. 20, 1993

[54] APPLANATION TONOMETER

[75] Inventor: Jörg Draeger, Hamburg, Fed. Rep. of Germany

[73] Assignee: Haag-Streit AG, Switzerland

[21] Appl. No.: 552,579

[22] Filed: Jul. 13, 1990

[30] Foreign Application Priority Data

Jul. 17, 1989 [CH] Switzerland ................ 02668/89

[51] Int. Cl.⁵ ............................................. A61B 3/16
[52] U.S. Cl. ................................................. 128/652
[58] Field of Search ............... 128/645, 646, 648, 652; 351/208

[56] References Cited

U.S. PATENT DOCUMENTS

| | | | |
|---|---|---|---|
| 3,446,061 | 5/1969 | Draeger et al. | 128/652 |
| 3,756,073 | 9/1973 | Lavallee et al. | 128/648 |
| 3,904,280 | 9/1975 | Tate, Jr. | |
| 3,934,462 | 1/1976 | Rende | |
| 4,095,859 | 6/1978 | Decker et al. | |
| 4,735,209 | 4/1988 | Foody | 128/652 |

FOREIGN PATENT DOCUMENTS 0315160  5/1989  European Pat. Off.
2175412A 11/1986  United Kingdom.

OTHER PUBLICATIONS

Zeimer et al., "An Instrument for Self-Measurement of Intraocular Pressure" IEEE Transac. on Biomed. Engineering, vol. BME-29, No. 3, Mar. 1982, pp. 178-183.

Primary Examiner—Randy C. Shay
Attorney, Agent, or Firm—Ostrolenk, Faber, Gerb & Soffen

[57] ABSTRACT

In the housing of the tonometer is disposed a forehead support capable to be displaced against the force of a spring and which can be locked rigidly in the housing in a determined position by a locking tooth which engages in an indentation. By means of a linear motor, a measuring body can be displaced toward the eye in order to measure in the known way the intracocular pressure. The result of the measurement is stored and indicated on a display. Due to the stable support of the tonometer by means of the forehead support and a full automatic control of the measuring process, the tonometer can serve for self tonometering, that is the person experimented upon, resp. the patient can proceed to the measure of its own intraocular pressure without any help from the outside. For this reason, the measurement can take place without important expenses, relatively often and at any times which guarantees a reliable diagnosis.

10 Claims, 3 Drawing Sheets

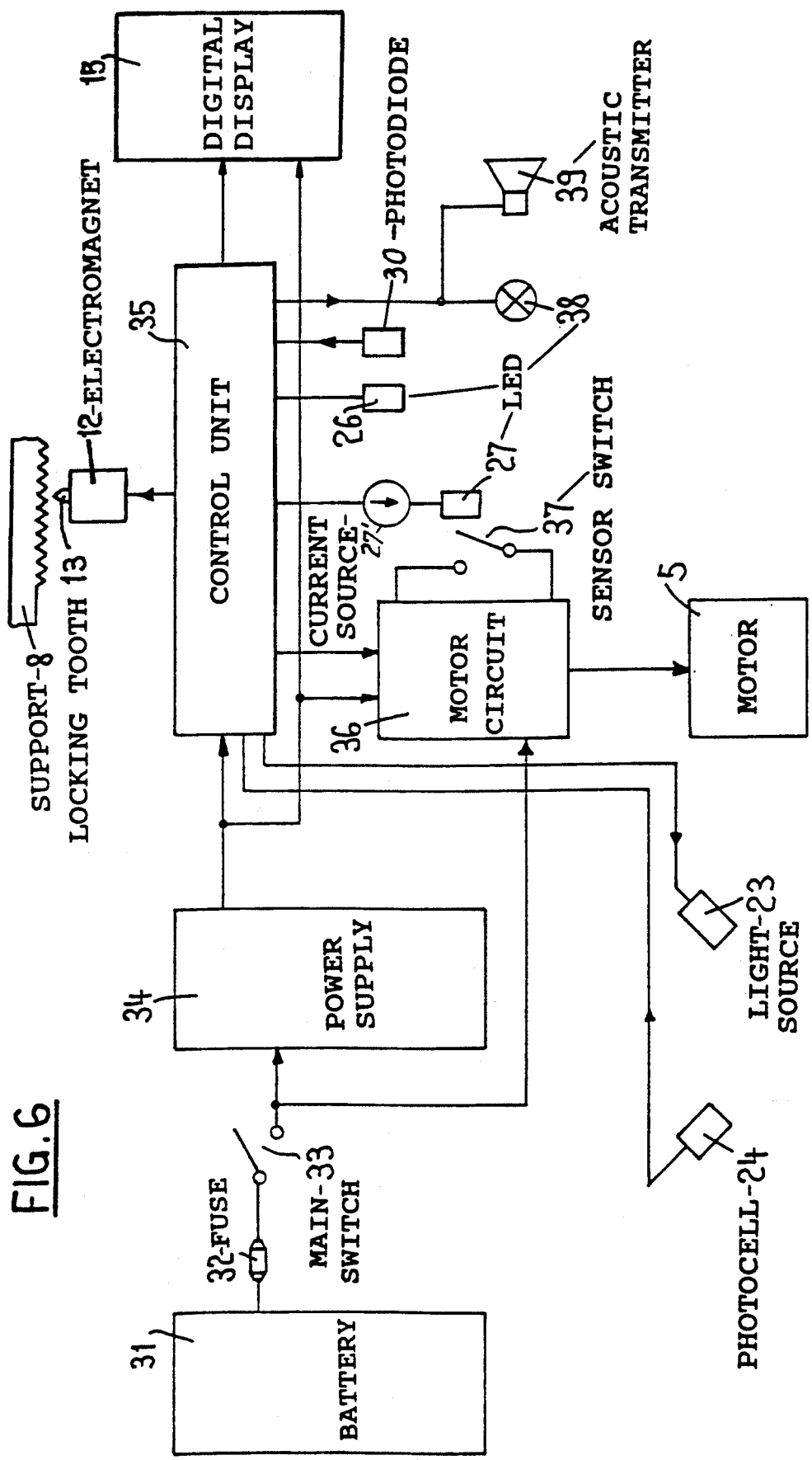

APPLANATION TONOMETER

BACKGROUND OF THE INVENTION

The present invention relates to an applanation tonometer with a measuring body capable to be put against the eye and with means for automatically detecting the pressure force of the measuring body as well as the applanation surface caused by said pressure force and for calculating the intraocular pressure from the measured quantities. Such a tonometer is known e.g. from WO87/01572. This one and generally all known applanation tonometers are so designed that they have to be operated by a corresponding instructed personal, more particularly by a doctor, in order to measure the eye pressure of the person experimented upon, i.e., the patient. Also when the proper measuring process is largely automatized and takes place electronically the handling with the tonometer is difficult if the measurement is to be correct and must take place without any danger of injury. New trends admit however that the intraocular pressure should be checked with regularity and relatively often, wherein it is important or necessary to detect the evolution of the pressure during one day. However, such a desired measurement executed at relatively shorts intervals of time is connected to insupportable expenses if not only the person experimented upon, resp. the patient but also an instructed auxiliary person has to participate.

SUMMARY OF THE INVENTION

It is an object of the present invention to create an applanation tonometer by means of which the person experimented upon, i.e., the patient himself can determinate its intraocular pressure. This problem is solved by an adjustable support for supporting the housing of the tonometer at a part of the visage nearby the eye, more particularly at the forehead. This permits to safely hold the tonometer in a determinate position with respect to the visage, i.e., the eye to be checked and due to the fact that the remaining process takes place fully automatically, the person experimented upon, i.e., the patient, has to hold the tonometer in the correct, measuring position for only a very short measuring time of about 1 sec and to excute otherwise no manipulations. The independence of auxiliary personal achieved is not only of a great economical signification but it permits also to execute measurements practically at any time. In this respect, the tonometer which is otherwise provided with a microprocessor for automatically conducting the measuring process can also be provided with a watch which can serve to remind by means of signals the person experimented upon to prescribed measurements times and/or to memorize the results of the measurements associated to the measurement times.

The tonometer may be further preferably provided with a system for detecting the distance of the measuring body from the eye. This system can be used while the tonometer is approaching, to lock the support when a determined distance is reached, in order to avoid a further advance of the tonometer and at the same time, as the case may be with a certain delay, to automatically release the measuing process. In this way, the person which tonometers himself obtain a further help and safety because otherwise it would be difficult to estimate a correct distance of the tonometer from the eye at the beginning of the measuring process and because otherwise one should fear to injure the eye by inattention.

BRIEF DESCRIPTION OF THE DRAWINGS

The invention will be now explained in more details by means of an example of execution with reference to the accompanying drawings.

FIG. 6 shows a block diagram schematic of the electrical equipment of the tonometer.

DETAILED DESCRIPTION OF THE INVENTION

Figure 1:
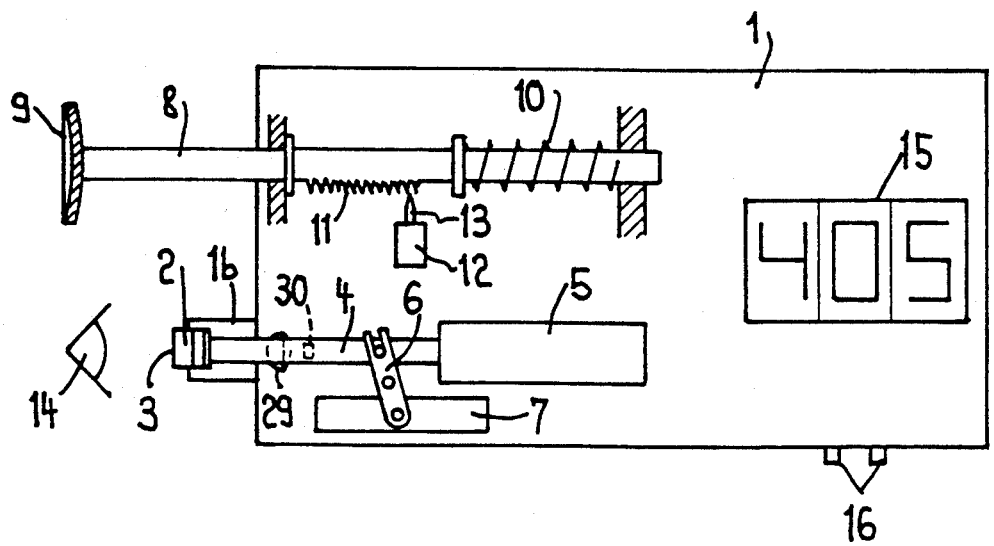
FIG. 1 is a pure schematic illustration of the essential parts of the tonometer.
Figure 2:
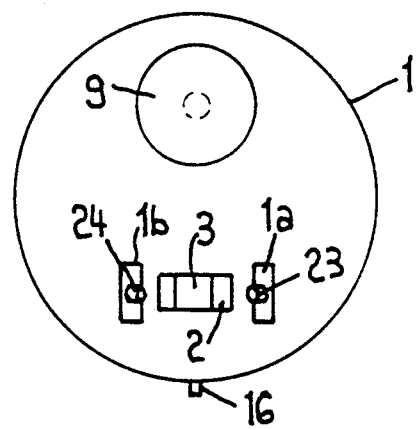
FIG. 2 is a front view of the tonometer.

FIGS. 1 and 2 show purely schematically the cylindrical housing 1 of the tonometer. This housing is so designed that it can be held easily in one hand. A measuring body 2 with a plane measuring surface 3 is fastened to a preferably interchangeable rod 4. The rod 4 is part of a during current linear motor 5 which comprises within a sufficient domain of adjustment a fully linear characteristic, that is exerting for a determined current, independently from the position of the measuring body 2, a determined force on the latter. The rod 4 is connected by a two armed lever 6 to a counterweight 7 which is guided in parallel with the rod 4 so that a full weight compensation and independence of the position is achieved. The tonometer may thus be held for measurement either horizontal or vertical or under any inclined position.

In the tonometer, is further guided a support 8 with a supporting plate 9. A pressure spring 10 holds the support 8 normally in a leading end position which is determined by an abutment as illustrated in FIG. 1. The support 8 comprises an indentation 11 in which a blocking tooth 13 can be engaged by means of an electromagnet 12 in order to lock the support 8 in a determined position in the housing 1. The support 8 with the supporting plate 9 can preferably be in form of a leading support, that is the plate 9 can be put against the forehead over the illustrated eye 14, in order to stabilize the position of the tonometer, resp. its measuring body 2 with respect to the eye 14.

The tonometer further comprises e.g. a digital display having three positions 15 which directly displays the intraocular pressure as will be explained later on.

Figure 3:
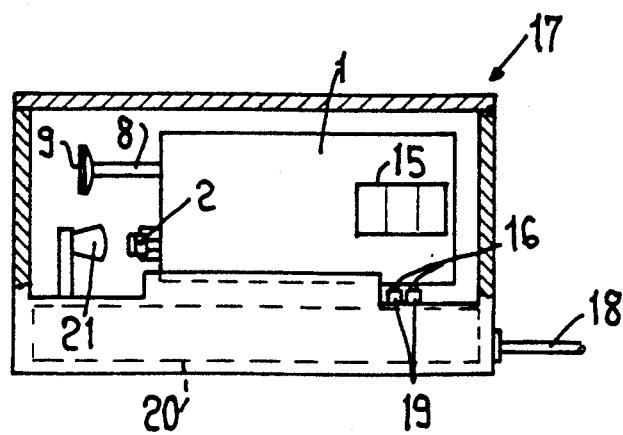
FIG. 3 shows the tonometer in a case intended for maintenance and travel.

Connecting contacts 16 are illustrated in the FIGS. 1 to 3.

FIG. 3 shows that the tonometer 1 can be fed by means of a mains connecting cable 18 in a maintenance and transporting case schematically illustrated, wherein the contacts 16 are in connection with the contacts 19, e.g. of a mains operated apparatus 20. It is admitted here that the electrical connection between the tonometer and a supply circuit in the case 17 serves only to charge rechargeable batteries for the supply of the tonometer ready to operate, when removed, outside of the case. The tonometer can also be continuously connected by means of a cable with a supply unit or directly with the mains.

As will be mentioned later on, important, complex connections can be provided between the tonometer and auxiliary equipment. In the case 17 is provided an ultraviolet source 21 which in the tonometer ready to use, is located directly opposite the measuring body 2 and which serves for the disinfection of the latter. It is clear that also other or further disinfection and/odor cleansing equipment may be present.

Figure 4:
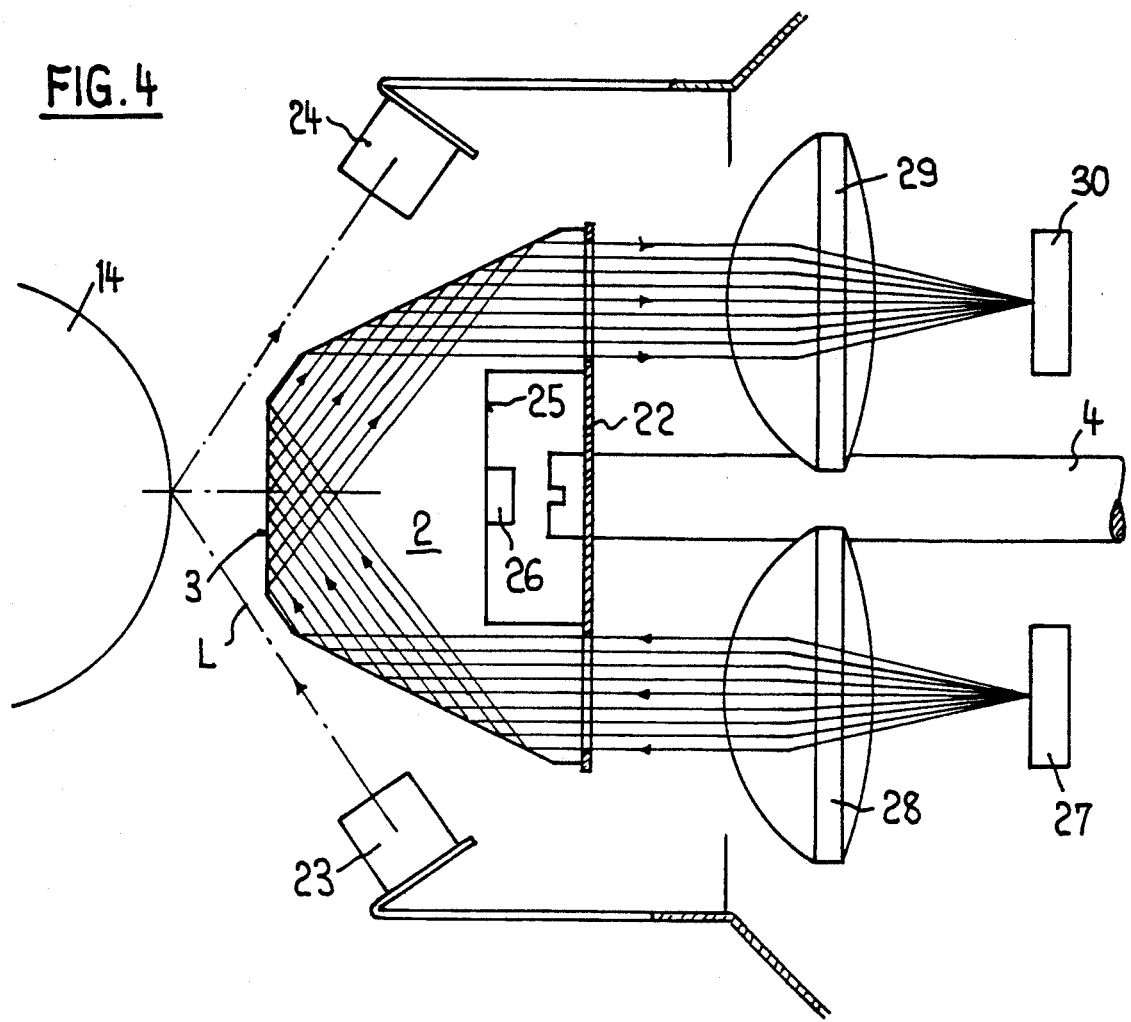
FIG. 4 shows optical elements of the tonometer for detecting the distance of the measuring body from the eye and for detecting the size of the surface of applanation.
Figure 5:
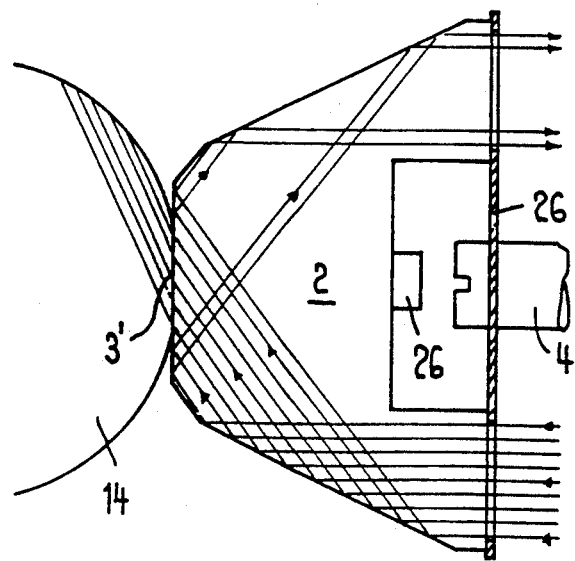
FIG. 5 shows an illustration corresponding to the tonometer of FIG. 4, however in contact with the eye.

The FIGS. 4 and 5 show the measuring body 2 at a greater scale. The measuring body is supported on a support 22 screwed to the rod 4. The housing 1 comprises appendices 1a and 1b of which only the posterior one is illustrated in FIG. 1 and to which is fastened on one side a source of light 23 (FIGS. 2 and 4) and on the other side an optical transducer, e.g. a photoelectric cell 24. In a recess 25 at the rear of the measuring body 2 consisting of a transparent material is provided a light emitting diode 26 which has the function of a fixing lamp for the correct orientation of the measuring body with respect to the eye 14. In the housing of the tonometer is provided on the one hand a light emitting diode 27 which preferably emit in the infrared range. A condenser 28 is associated to the light emitting diode so that a homogeneous beam of parallel rays from the condenser 28 enters from behind in the measuring body. This beam of rays is totally reflected at an inclined flank of the measuring body and delivered to the plane measuring surface 3 of the measuring body. At this place, it is again totally reflected, when the measuring body according to FIG. 4 is removed from the eye and it arrives over the opposite inclined flank of the measuring body through a convergent lens 29 on a photoelectric transducer 30, e.g. a photodiode.

As illustrated in FIG. 4, a ray of light L from the light source 23 is so reflected that is can enter in the phototransducer 24 through a relatively narrow screen of the latter. This path of the rays is only possible for a determined distance of the measuring body, i.e., of the parts 23 and 24 from the eye. Thus, this arrangement permits to recognize when the measuring body has reached a determined distance from the eye during the slow approach of the tonometer towards the eye. When this distance is reached, the electromagnet 12 is excited and it introduces the locking tooth 13 in the indentation 11 of the support 8, so that the latter is rigidly locked in the housing 1. It is clear that also other electrically controlled locking devices may be provided for locking the support.

It is admitted that when the measuring body 2 is removed from the eye, all the light entering into the measuring body is totally reflected and arrives on the photodiode 30. If however in accordance with FIG. 5, the measuring body is in contact against the eye, it follows that on the surface of contact or applanation surface 3', there is no reflection or only a weak one because an important part of the light enters into the eye 14. Consequently only a diminished part of light corresponding to the applanation surface comes out of the measuring body and enters into the photodiode 30 as shown in FIG. 5. The photodiode 30 delivers then a signal which is a measure for the size of the applanation surface 3'. This signal can also serve to calculate the size of the applanation surface 3' by means of a calculator, i.e., a microprocessor. Similarly, the direct current fed to the linear motor 5 can serve to determine the magnitude of the force exerted by the measuring body against the eye. The two parameters permit finally to calculate the intraocular pressure and to display it on the display 15.

FIG. 6 shows a block diagram schematic of the essential parts of the electrical equipment of the tonometer. The schematically illustrated battery 31 feeds through a fuse 32 and a main switch 33 a supply unit 34, which provides the different necessary voltages. The central part of the circuit is a control unit 35 with a microprocessor which monitors and evaluate all above mentioned controls and measurements. The elements already described are designated in FIG. 6 by the same numbers as in the other Figures and they will not be explained further. A sensor switch 37 is associated to a motor circuit 36 for the control of the motor 5, this sensor switch permitting to arbitrarily switch on the motor. In addition to the already described units, an indicator unit with a light emitting display 38 and/or an acoustical signal transmitter 39 is connected to the control unit 35. The light emitting diode 27 is fed by a constant current from a source of current 27'.

For the measurement of the intraocular pressure, one proceeds as follows:

First of all, the main switch 33 is switched on so that all circuits are energized. The fixing lamp 26, the light emitting diode 27 and the light source 23 are also switched on. However, the sensor switch 37 remains at first open so that the motor 5 remains switched off. The tonometer is now displaced with its measuring body toward the eye and with the support 8 against the forehead, the fixing lamp 26 being continuously observed and the tonometer being oriented correspondingly and centered on the eye. When the forehead support 8, 9 comes into contact, with the forehead of the person experimented upon, i.e., the patient, this support is introduced into the housing of the tonometer against the pressure of the spring 10. The measuring body 2 with the light source 23 and the photocell 24 comes nearer the eye (FIG. 4) until the light beam L is reflected directly in the photocell 24 by the surface of the eye which is the case for a determined distance of e.g. 10 to 15 mm between the measuring surface 3 of the measuring body and the eye. The signal delivered from the photocell 24 to the control unit 35 causes on the one hand the excitation of the electromagnet 12 and the engagement of the locking tooth 13 in the indentation of the support 8. In this way, the support 8 is locked in the housing of the tonometer which prevents a further manual displacement of the tonometer against the eye and guarantees a safe, rigid support of the tonometer on the forehead. At the same time, the display 38 is illuminated and/or the signal transmitter 39 sounds and indicates to the person experimented upon that the ready position is attained and that the measurement can start. The person experimented upon then actuates the sensor switch 37 so that the motor is switched on and directs the measuring body with a predetermined speed towards the eye 14. The applanation surface is then continuously detected in the manner described and when the prescribed applanation, e.g. with a diameter of 3.06 mm is attained, the measuring force applied by the motor 5 is instantaneously detected and stored and it serves to the calculation of the intraocular pressure. The measurement is then terminated, the motor 5 is switched off and a luminous or acoustical signal can be delivered in order to indicate the end of the measurement. The tonometer is then removed and accomodated in the case 17 in which its batteries are charged and the measuring body 2 can be disinfected in the ultraviolet light. It is clear that also other measures for cleaning and/or the disinfection of the measuring body can be applied. The feedback of the measuring body in its initial position can take place either through reversing of the direction of the current in the motor or through a weak pull back spring the force of which being taken into account in the measurement. The determined and stored result of the measurement is then indicated by the display 15 and it can be read. As mentioned, this result can be continuously stored and it can be read and evaluated later on together with many other results of measurements. As mentioned, to each result of measurement can be associated and stored a measuring time. The transmission of individual results of measurement and as the case may be of measuring times can also take place at each set in of the tonometer in the case 17 in which matter the electronic of this case can be designed for storing many results of measurements. Finally, it could also be provided a printer which summarises the results in tabular form so that a late evaluation would be additionally facilitated. From the stored values, diagrams can also be produced which illustrate the evolution in the time of the measured eye pressure.

The example of execution illustrated and described above is explicitly to be seen as an example. Different elements may be differently designed. Instead of a linear motor, e.g. a moving coil system can be provided for the drive of the measuring body. During the measurement, the influence of the liquid of the tears can be considered, e.g. in the sense of the above mentioned WO87/01572. An other measuring system for detecting the applanation surface can also be provided.

The described measurement cannot be an absolute one and, as the case may be, it is necessary that at the time of switching on of the device, a test program runs and that a self calibrating takes place. In this case, the above mentioned ready signal can indicate that as well the correct measuring position of the tonometer is attained as also that the test program is successfully terminated. From similar considerations, it is desired to mount the analog-digital conversion the most possible in the neighbourhood of the measuring places, that is more particularly to associate immediately the photodiode 30 to an analog-digital wandler.

As mentioned, the time of the measurement of the intraocular pressure is essential because, from the experience, this pressure can vary very strongly in the course of one day. If the tonometer, i.e., the case 17 is provided with a watch, measurement times could also be programmed to which then a corresponding signal would sound which would be a incitation for the person experimented upon, i.e., the patient to execute the measurement.

If the tonometer is equipped with rechargeable batteries, these ones should be so designed that they could be exchanged at any time with non-rechargeable batteries if necessary.

While in the example of execution a cylindrical housing was presented for the sake of simplicity, other appropriate forms of housing could be provided, e.g. a housing in form, of a T with a handle perpendicular to the measuring direction in which handle parts of the device, e.g. the mentioned moving coil drive, could be housed.

Preferably, the measuring body can be so connected with the rod 4 that it can easily be replaced.

The mentioned main switch 33 could also be automatically closed when the tonometer is taken out of the case 17, a pin acting on a key of the main switch being provided in the case.

Likewise, the sensor switch 37 can be eliminated when after the nominal distance of the tonometer from the eye is attained, as the case may be with an adequate deceleration, the motor is automatically switched on by the microprocessor.

I claim:
1. An applanation tonometer, comprising:
 a) a housing;
 b) a measuring body for engagement with an eye whose intraocular pressure is to be measured, the measuring body being movably mounted to the housing;
 c) an adjustable support for the housing;
 d) means for adjusting the housing relative to the support to position the measuring body at a predetermined distance from the eye;
 e) means for automatically detecting when the predetermined distance has been achieved;
 f) means for automatically locking the support when the predetermined distance has been achieved;
 g) means for moving the measuring body to cause the measuring body to apply force to the eye to applanate the eye;
 h) means for measuring the amount of applanation;
 i) means for measuring the force applied to the eye; and
 j) means responsive to means h) and i) for determining the intraocular pressure of the eye.

2. A tonometer according to claim 1, wherein means d) includes a spring and wherein means f) is an electromechanical locking means.

3. A tonometer according to claim 1, wherein means e) comprises a light source and a photoelectric transducer arranged with respect to one another such that when the predetermined distance has been achieved, a beam of light from the light source is reflected by the eye to the transducer.

4. A tonometer according to claim 1, wherein means i) comprises a microprocessor.

5. A tonometer according to claim 4, further including display means for displaying the results of the measurements made by means h) and i) and the determination made by means j).

6. A tonometer according to claim 5, wherein the display means includes a printer.

7. A tonometer according to claim 1, further comprising a watch for indicating the time of a measurement, display means for displaying the results of a measurement and memory means for storing the results of a measurement and the time thereof.

8. A tonometer according to claim 1, in combination with maintenance and transport case means for receiving the housing, the case means having a disinfection device for selectively disinfecting the measuring body when the housing is in the case means.

9. A tonometer according to claim 8, wherein the disinfection device comprises an ultraviolet radiator.

10. A tonometer according to claim 9, wherein the case means includes means for receiving a battery, a memory for storing the result of a measurement and a printer for the result of a measurement.

* * * * *